(12) United States Patent
Lampkin et al.

(10) Patent No.: US 11,822,073 B2
(45) Date of Patent: Nov. 21, 2023

(54) VISION IMPROVEMENT UTILIZING COMPUTER DISPLAYS

(71) Applicant: International Business Machines Corporation, Armonk, NY (US)

(72) Inventors: Valerie Lampkin, Woodstock, GA (US); Alice-Maria Marascu, Dublin (IE); Maeve O'Reilly, Wicklow (IE); Clea Zolotow, Key West, FL (US)

(73) Assignee: International Business Machines Corporation, Armonk, NY (US)

( * ) Notice: Subject to any disclaimer, the term of this patent is extended or adjusted under 35 U.S.C. 154(b) by 1603 days.

(21) Appl. No.: 15/855,125

(22) Filed: Dec. 27, 2017

(65) Prior Publication Data
US 2019/0146215 A1 May 16, 2019

Related U.S. Application Data

(63) Continuation of application No. 15/814,636, filed on Nov. 16, 2017, now Pat. No. 11,131,849.

(51) Int. Cl.
*G02B 27/00* (2006.01)
*A61B 3/024* (2006.01)
(Continued)

(52) U.S. Cl.
CPC ........ *G02B 27/0093* (2013.01); *A61B 3/0025* (2013.01); *A61B 3/0033* (2013.01);
(Continued)

(58) Field of Classification Search
CPC . G02B 27/0093; A61B 3/0025; A61B 3/0033; A61B 3/0041; A61B 3/0066;
(Continued)

(56) References Cited

U.S. PATENT DOCUMENTS 8,668,334 B2    3/2014   Krenik
11,131,849 B2 *  9/2021   Lampkin ............... A61B 3/024
(Continued)

OTHER PUBLICATIONS

Mell et al., "The NIST Definition of Cloud Computing", National Institute of Standards and Technology, U.S. Dept. of Commerce, NIST Special Publ. 800-145, Sep. 2011, 7 pages.
(Continued)

*Primary Examiner* — Marin Pichler
(74) *Attorney, Agent, or Firm* — Gavin Giraud; Rachel L. Pearlman, Esq.; Heslin Rothenberg Farley & Mesiti P.C

(57) ABSTRACT

A method, computer program product, and system includes a processor(s) utilizing the image capture device to track eye movements of a user interacting with a display communicatively coupled to the one or more processors, the image capture device continuously collecting image data. The processor(s) determines, based on analyzing the collected image data, a probability of whether a user may be experiencing a vision-related issue. Based on the probability being within a given pre-determined range, the processor(s) identifies the vision-related issue experienced by the user. The processor(s) generates, based on the vision-related issue, a two dimensional visual exercise to address the vision-related issue for performance by the user. The processor(s) deploys a graphical user interface to the display, where the graphical user interface comprises the visual exercise. The processor(s) provides the visual exercise to the user via the graphical user interface.

13 Claims, 7 Drawing Sheets

(51) Int. Cl.
  *A61B 3/00* (2006.01)
  *A61B 3/113* (2006.01)
(52) U.S. Cl.
  CPC .......... *A61B 3/0041* (2013.01); *A61B 3/0091* (2013.01); *A61B 3/024* (2013.01); *A61B 3/113* (2013.01)
(58) Field of Classification Search
  CPC ....... A61B 3/0091; A61B 3/024; A61B 3/113; G06F 3/048; G06F 3/013
  USPC .......................... 351/200, 203, 205, 206, 209
  See application file for complete search history.

(56) References Cited

U.S. PATENT DOCUMENTS

| | | | | |
|---|---|---|---|---|
| 2015/0257967 | A1* | 9/2015 | Simmons | G16H 50/20 434/236 |
| 2017/0000454 | A1 | 1/2017 | Samec et al. | |
| 2017/0119245 | A1 | 5/2017 | Bartlett et al. | |
| 2017/0351326 | A1* | 12/2017 | Aarts | G06F 3/013 |

OTHER PUBLICATIONS

List of IBM Patents or Patent Applications Treated as Related, Feb. 1, 2018, 2 pages.

Lampkin et al., "Vision Improvement Utilizing Computer Displays," U.S. Appl. No. 15/814,636, filed Nov. 16, 2017, pp. 1-41.

* cited by examiner

VISION IMPROVEMENT UTILIZING COMPUTER DISPLAYS

BACKGROUND

Individuals may spend extended amounts of time staring at computer screens as part of their employment. Extended hours in front of a computer display can result in eye strain, i.e., asthenopia. The human eye has six muscles allowing the eye rotation and reading content on a computer screen does not involve the usage of all six muscles, but instead, only two of the muscles, which can lead to eye tiredness and convergence insufficiency.

SUMMARY

Shortcomings of the prior art are overcome and additional advantages are provided through the provision of a method for automatically improving vision of a user utilizing a computer display. The method includes, for instance: utilizing, by one or more processors, an image capture device to track eye movements of a user interacting with a display communicatively coupled to the one or more processors, the image capture device continuously collecting image data; determining, by the one or more processors, based on analyzing the collected image data, a probability of whether a user may be experiencing a vision-related issue; based on the probability being within a given pre-determined range, identifying, by the one or more processors, the vision-related issue experienced by the user; generating, by the one or more processors, based on the vision-related issue, a two dimensional visual exercise to address the vision-related issue for performance by the user; deploying, by the one or more processors, a graphical user interface to the display, wherein the graphical user interface comprises the visual exercise; and providing, by the one or more processors, the visual exercise to the user via the graphical user interface.

Shortcomings of the prior art are overcome and additional advantages are provided through the provision of a computer program product for automatically improving vision of a user utilizing a computer display. The computer program product comprises a storage medium readable by a processing circuit and storing instructions for execution by the processing circuit for performing a method. The method includes, for instance: utilizing, by the one or more processors, an image capture device to track eye movements of a user interacting with a display communicatively coupled to the one or more processors, the image capture device continuously collecting image data; determining, by the one or more processors, based on analyzing the collected image data, a probability of whether a user may be experiencing a vision-related issue; based on the probability being within a given pre-determined range, identifying, by the one or more processors, the vision-related issue experienced by the user; generating, by the one or more processors, based on the vision-related issue, a two dimensional visual exercise to address the vision-related issue for performance by the user; deploying, by the one or more processors, a graphical user interface to the display, wherein the graphical user interface comprises the visual exercise; and providing, by the one or more processors, the visual exercise to the user via the graphical user interface.

Methods and systems relating to one or more aspects are also described and claimed herein. Further, services relating to one or more aspects are also described and may be claimed herein.

Additional features are realized through the techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

Figure 1:
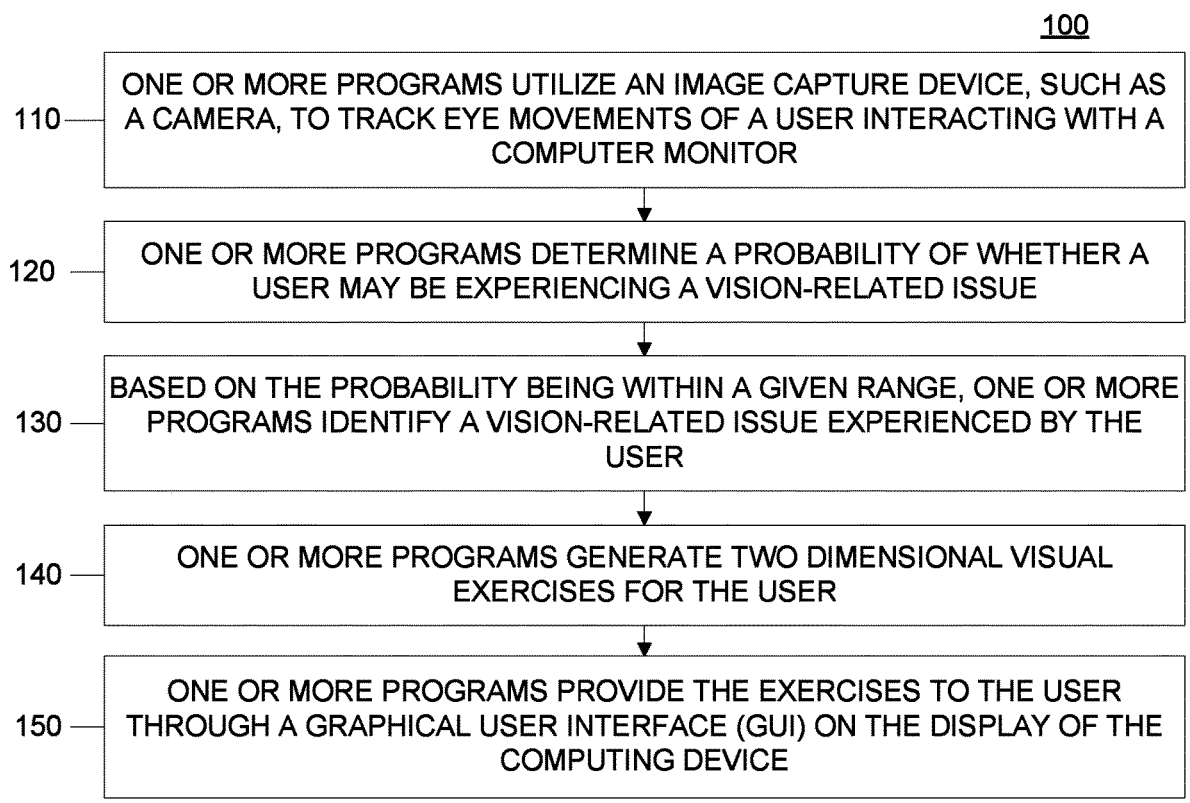
FIG. 1 is a workflow illustrating certain aspects of an embodiment of the present invention.

The accompanying figures, in which like reference numerals may refer to identical or functionally similar elements throughout the separate views and which are incorporated in and form a part of the specification, further illustrate the present invention and, together with the detailed description of the invention, serve to explain the principles of the present invention. As understood by one of skill in the art, the accompanying figures are provided for ease of understanding and illustrate aspects of certain embodiments of the present invention. The invention is not limited to the embodiments depicted in the figures.

Figure 5:
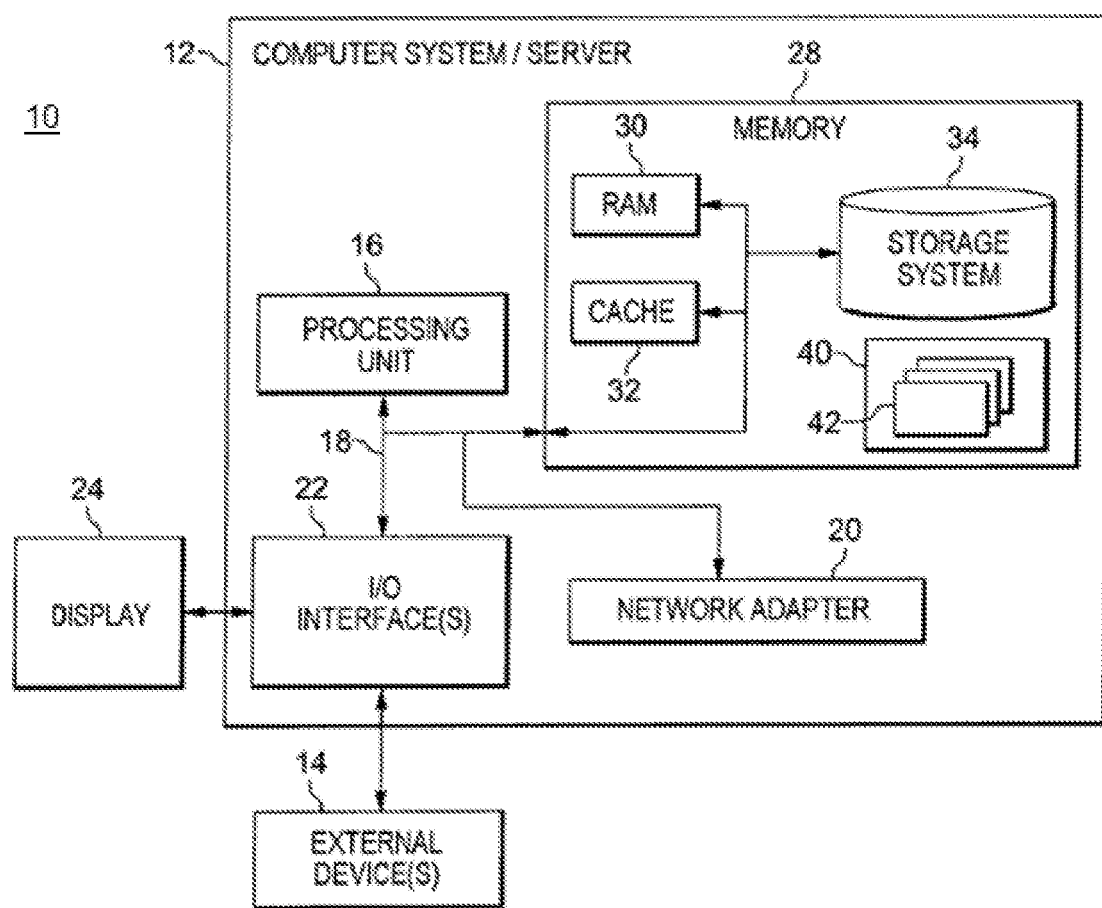
FIG. 5 depicts one embodiment of a computing node that can be utilized in a cloud computing environment.

As understood by one of skill in the art, program code, as referred to throughout this application, includes both software and hardware. For example, program code in certain embodiments of the present invention includes fixed function hardware, while other embodiments utilized a software-based implementation of the functionality described. Certain embodiments combine both types of program code. One example of program code, also referred to as one or more programs, is depicted in FIG. 5 as program/utility 40, having a set (at least one) of program modules 42, may be stored in memory 28.

Embodiments of the present invention include a computer-implemented method, a computer program product, and a computer system that includes an image capture device, such as a camera, that monitors the eye movements of an individual utilizing a computer display. In some embodiments of the present invention, the image capture device may be embedded in the computer display. Based on monitoring the eye movement of the user, one or more programs executed by at least one processing device (communicatively coupled to the computer display and the image capture device), determine that an event has occurred. Based on this determination, the one or more programs provide a visual experience, through the computer display, to the user, which includes eye exercises. Thus, the one or more programs generate a graphical user interface (GUI) on the computer screen to provide (automatically) eye exercises to the user. In some embodiments of the present invention, the event is the onset of visual fatigue, or repetitive eye movements that could lead to fatigue. The graphical user interface may provide the user with visuals that provide a two dimensional representation of known eye exercises, presently provided exclusively as paper charts, including but not limited to, representations of Rizzi charts, which can be utilized to train fusion in divergence or convergence. The one or more programs may generate a two dimensional representation that provides exercises that incrementally reduce a distance from a current focal of a user (who is experiencing a vision issue) to the correct focal point (i.e., the focal point utilized by a user who is not experiencing a vision issue).

In some embodiments of the present invention, the event may be a lack of convergence. Convergence refers to focusing the eyes to a point which is in front of the visual exercise, which in existing approaches appear on physical paper cards, but is rendered in a graphical user interface (GUI) by one or more programs in an embodiment of the present invention. This point of focus in front of the exercise (e.g., imaginary, the tip of the nose or of a pen) is between the eyes of the user and the medium upon which the exercise appears. The object rendering the exercise (e.g., the sheet or the computer screen) is situated between the eyes of the user and the point of focus (e.g., a far object).

In some embodiments of the present invention, the one or more programs determine that an event has occurred by identifying, based on the monitoring of eye movement by the image capture device, that the user observing the computer screen is experiencing a vision-related issue. By identifying the particular vision-related issue, the one or more programs can select an eye exercise that would address this issue. Upon selecting an exercise, the one or more programs convert the exercise, which was previously limited to a physical sheet of paper, to a two dimensional representation that can be rendered on the computer screen. The one or more programs render the converted exercise on the computer screen as a graphical user interface (GUI).

Events in embodiments of the present invention that are identified by the one or more programs encompass a variety of perceived vision issues as well as behaviors of the user that could potentially lead to vision issues. For example, one or more programs in an embodiment of the present invention may compute (and continually update) a user score, and a qualifying event that prompts the one or more programs to generate and launch eye exercises would be the score exceeding a predetermined threshold. To generate a score, the one or more programs may utilize parameters, including but not limited to, the consecutive time spent in front of a screen by the user without taking a break, the type of activity engaged in by the user, through the GUI on the computer screen, the time of day the user is engaging with a GUI on the computer screen, and the previous history of the user's utilization of the computer screen and/or eye movements during utilization of the computer screen. As aforementioned, in some embodiments of the present invention, an event has occurred when one or more program determines that the user is experiencing a vision-related issue. For example, by utilizing the image capture device to observe eye movements of a user, the one or more programs may determine that a current focal point of the user differs from a focal point located at the level of the screen, which would be a correct focal point for a user who is not experiencing a vision-related issue.

Embodiments of the present invention are inextricably tied to computing and provide advantages over existing approaches to addressing the issue of eye strain caused by utilization of computer screens/displays. Embodiments of the invention are linked to computing at least because they address an issue that is experienced during computing sessions and provide an approach that by utilizing a unique combination of software and hardware (i.e., a computer display with an image capture device, optionally integrated into the computer display, and one or more processors executing one or more programs). Unlike existing eye exercises, which are provided by two dimensional cards, when a user decides that he or she is experiencing a condition that would benefit from using the cards, in embodiments of the present invention, one or more programs automatically determine that an individual is either experiencing a vision issue or may experience a vision issue based on observed behaviors, and the one or more programs automatically provide the user with two dimensional vision exercises, to address the observed issue.

Embodiments of the present invention include various aspects that provide improvements over existing methods of providing eye exercises to individuals experiencing vision issues including fatigue, eye strain, and convergence insufficiencies. The most common existing method of addressing vision-related issues is a user manually utilizing two-dimensional printed paper charts, which include eye exercises. However, a user does not necessarily have these charts and/or a user may not be aware of he or she should use the chart to mitigate vision-related issues (e.g., a user may utilize the charted exercises when they are not necessary and/or the user may fail to utilize the exercises when they are necessary). A user may also be unaware of what exercises he or she should utilize to mitigate an issue experienced. Although eye strain and muscle imbalances may cause convergence insufficiency and this issue is treatable with eye exercises, existing methods (i.e., physical cards), unlike embodiments of the present invention, do not interactively prompt users of computer screens to complete the correct exercises to address the vision-related issue experienced by the user.

FIG. 1 is a workflow 100 depicting certain aspects of some embodiments of the present invention. As illustrated in FIG. 1. In some embodiments of the present invention, one or more programs: 1) monitor eye movements of a user of a computing device while the user interacts with the display of the device (110); 2) determine a probability of whether a user may be experiencing a vision-related issue (120); 3) based on the probability being within a given range, identify a vision-related issue experienced by the user (130); 4) generate two dimensional visual exercises for the user (140); and 5) provide the exercises to the user through a graphical user interface (GUI) on the display of the computing device (150).

Returning to FIG. 1, to monitor eye movements of a user of a computing device while the user interacts with the display of the device, in an embodiment of the present invention, one or more programs executed by one or more processors utilize an image capture device, such as a camera, to track eye movements of a user interacting with a computer monitor (e.g., screen, display, etc.) (110). The image capture device is communicatively coupled to the one or more processors. The one or more programs receive data from the image capture device indicating the eye movements of the user, when observing the computer monitor.

To determine a probability of whether a user may be experiencing a vision-related issue, the one or more programs generate a score representing the eye movements of the user (120). This score represents a likelihood that the individual utilizing the computing device is experiencing a vision-related issue. The one or more programs utilize the score to determine a likelihood that the user is experiencing an issue (e.g., eye strain), where a score above a predetermined threshold indicates that the user may be experiencing eye strain. In some embodiments of the present invention, the one or more programs compute the score based on observed (by the image capture device) behaviors of the user, including but not limited to, continuous time spent in front of the computer monitor by the user, the type of activity the user is engaged in while utilizing the computer monitor, the time of day in which the user is utilizing the computer monitor, and/or personal information related to the user (e.g., historical medical prescription information). The type of activity is a parameter of the score in some embodiments of the present invention because different activities are more or less taxing on eye muscles. For example, a passive activity, such as reading an article on screen, may utilize fewer muscle movements than a more active activity, such as typing in a document editing program. The time of day that a user interacts with a computer monitor is useful as a parameter in computing a score because a user's eyes may be more or less tired depending on the time of day (e.g., a user's eye muscles may be more fatigued in the morning than in the evening).

Based on determining that the score is above a predetermined threshold, (i.e., the user is likely to be experiencing a vision-related issue or at risk for an issue) the one or more programs identify the vision-related issue experienced by the user (130). By identifying aspects of a vision-related issue, the one or more programs can determine what exercises would be effective in addressing the issue. In order to identify the vision-related issue, in an embodiment of the present invention, one or more programs receive data from the image capture device (e.g., the camera integrated into the computer monitor) indicating the eye movements of the user when observing the computer monitor. The one or more programs compute observed eye movements to identify a vision-related issue experienced by the user. For example, the one or more programs may observe the eye movements of the user and to determine convergence insufficiency and which of the six muscles of the eye needs to be straightened into order to correct convergence. The one or more programs may compute a distance between a current focal point of the user (based on the observed eye movements relative to the computer monitor) and a correct focal point (e.g., located at the screen level), to determine the vision-related issue experienced, based on the distance.

The one or more programs generate two dimensional visual exercises for the user (140) and provide the exercises to the user through a graphical user interface (GUI) on the display of the computing device (150). In some embodiments of the present invention, the display upon which the one or more programs provide the exercises is the same as the display that the image capture device monitors the user's interaction with. Thus, the one or more programs generate a GUI that includes a two dimensional representation of visuals that stimulate eye exercises.

To configure a particular exercise for a given user, the one or more programs compute the distance between the current focal point of the user and the correct focal point. The one or more programs generate exercises that utilize the current focal point and the correct focal point. For example, the one or more programs generate an exercise that starts with the current (incorrect) point and works to change the point of focus of the user by decreasing the distance between the focal points, gradually. By decreasing the distance, the focus of the user can be shifted from the current focal point, at least closer to the correct focal point, e.g., to correct convergence.

In order to provide the exercises generated to the user, the one or more programs may utilize existing methods for transformation of physical charts and cards (e.g., three dimensional objects) utilized as vision exercises, into two dimensional images, that can be rendered on a computer screen and utilized to exercise eye muscles.

In some embodiments of the present invention, the one or more programs pause any application the user is interacting with on the computer screen before executing the visual exercises and only resume the application once the user had completed the exercises. The one or more programs may determine that an exercise is complete by continuing to score the user and terminate the exercise when the user's score no longer exceed the predetermined threshold. The one or more programs monitor the user, utilizing data from the image capture device, while the user performs the exercise, and resumes the application the user was utilizing before the one or more programs initiated the exercises.

Figure 2:
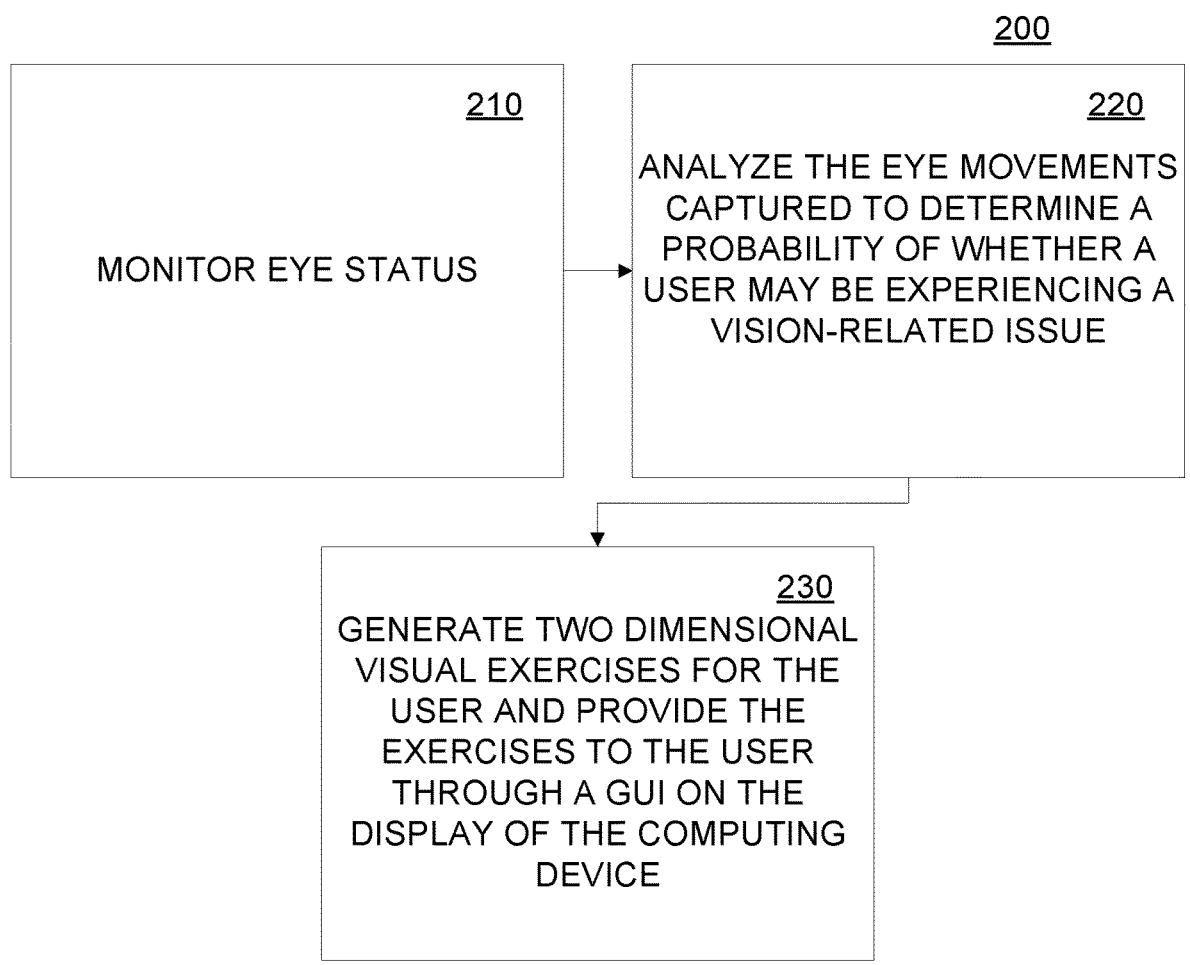
FIG. 2 is an illustration of certain aspects of an embodiment of the present invention.

FIG. 2 is a modular representation 200 of various aspects of some embodiments of the present invention. The modular representation is provided in order to illustrate functionality of various embodiments of the present invention and is not to impose any technical limitations on the implementations of the aspects in hardware and software. In FIG. 2, the one or more programs are separated into a first component 210, a second component 220, and a third component 230. The first component 210 is comprised of one or more programs that monitor the movements of a user's eyes. As discussed above, the one or more programs may utilize an in-screen image capture device, such as an integrated camera, to monitor eye movement of a user interacting with the screen. A second component 220 includes one or more programs that analyze the eye movements captured to determine a probability of whether a user may be experiencing a vision-related issue (e.g., scoring the movements of the user) and based on the probability being within a given range, identify a vision-related issue experienced by the user. The third component 230 includes one or more programs that generate two dimensional visual exercises for the user and provide the exercises to the user through a GUI, on a display of the computing device. Generating the two dimensional exercises, generating a GUI, and providing the exercises through the GUI, can be understood as adapting screen text into an exercise mode.

Figure 3:
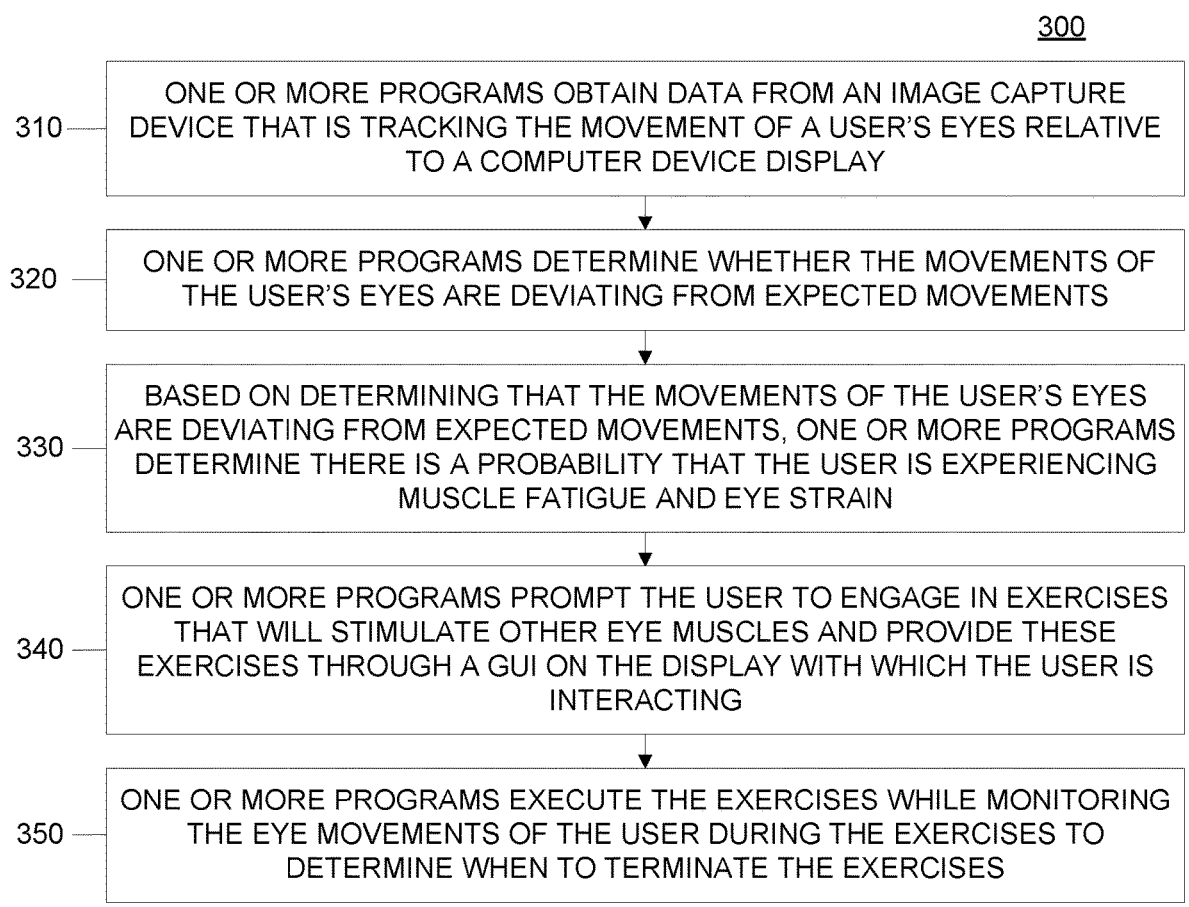
FIG. 3 is a workflow illustrating certain aspects of an embodiment of the present invention.

FIG. 3 is a workflow 300 that illustrates certain aspects of some embodiments of the present invention. In an embodiment of the present invention, one or more programs executed by at least one processor obtain data from an image capture device that is tracking the movement of a user's eyes relative to a computer device display (310). The image capture device may be embedded into the display in order to track the movements of the user's eyes effectively and accurately.

The one or more programs determine whether the movements of the user's eyes are deviating from expected movements (320). In some embodiments of the present invention, the one or more programs make this determination by comparing an expected position/motion of the user's eyes with an historical analysis of the user's eye movements, based on identifying the user. To identify the user, the one or more programs may utilize high security methods, such as employing a retinal scan through the image capture device and/or obtaining identifying information about the user from the application the user is interacting with (e.g., the user's login information to the operating system). The one or more programs may determine that the user's movements are a deviation based on factors including, but not limited to, the user's pupils not moving synchronous to each other, discovering a distance existing between a current focal point of the user (based on the observed eye movements relative to the computer monitor) and a correct focal point (e.g., located at the screen level), observing behaviors of the user that could potentially lead to vision issues (e.g., continuous time spent in front of the computer monitor, a type of activity, a time of day in which the user is utilizing the computer monitor), and/or personal information related to the user (e.g., historical medical prescription information).

Based on determining that the movements of the user's eyes are deviating from expected movements, the one or more programs determine there is a probability that the user is experiencing muscle fatigue and eye strain (330). As discussed earlier, the one or more programs may determine this probability based on scoring parameters such as the eye movements of the user, the physical setting/conditions in which the user is interacting with the display, the medical history of the individual, and/or the user's historical usage patterns for the computing device and display. In some embodiments of the present invention, the one or more programs compute a score that reflects the probability the user is experiencing a vision issue based on time spent by the user in front of the screen without a break, the type of activity the user is engaged in, the time of the day the user is interacting with the display, and the previous history of the user (screen usage history and/or medical history).

The one or more programs prompt the user to engage in exercises that will stimulate other eye muscles and provides these exercises through a GUI on the display with which the user is interacting (340). The one or more programs may determine that the user would benefit from interacting specifically with vision improvement cards, such as Rizzi cards, and the one or more programs may initiate exercises that provide two dimensional representations of the exercises in these cards on the computer display. In providing the exercises, the one or more programs may render objects from vision improvement cards. In rendering these objects, the one or more programs transform the content of the physical cards to two dimensional screen text/figures.

In some embodiments of the present invention, the one or more programs execute the exercises while monitoring the eye movements of the user during the exercises to determine when to terminate the exercises (350). The one or more programs continuously monitor the eye movements of a user utilizing the image capture device. The one or more programs utilize the image data to determine when a distance between the focal point of the user (i.e., an incorrect focal point) approaches an anticipated focal point (e.g., a correct focal point). The distance change utilized by the one or more programs to determine the success of the exercise may be based on historical data related to the vision of the user. For example, a user with certain vision issues cannot be corrected, through exercises, to the anticipated focal point, but progress can be made through the exercises that indicates an improvement enabling the one or more programs to complete generation and display of visual exercises. In some embodiments of the present invention, the one or more programs track the frequency with which the user utilizes the exercises, on a temporal basis (daily, weekly, monthly, etc.), and estimates the strength of the eye muscles of the user over time. In some embodiments of the present invention, if the one or more programs determine a lack of improvement based on monitoring eye movements over time, during, before, and/or after eye exercises, the one or more programs may alert the user that he or she may wish to visit an optician for consultation and vision support.

Figure 4:
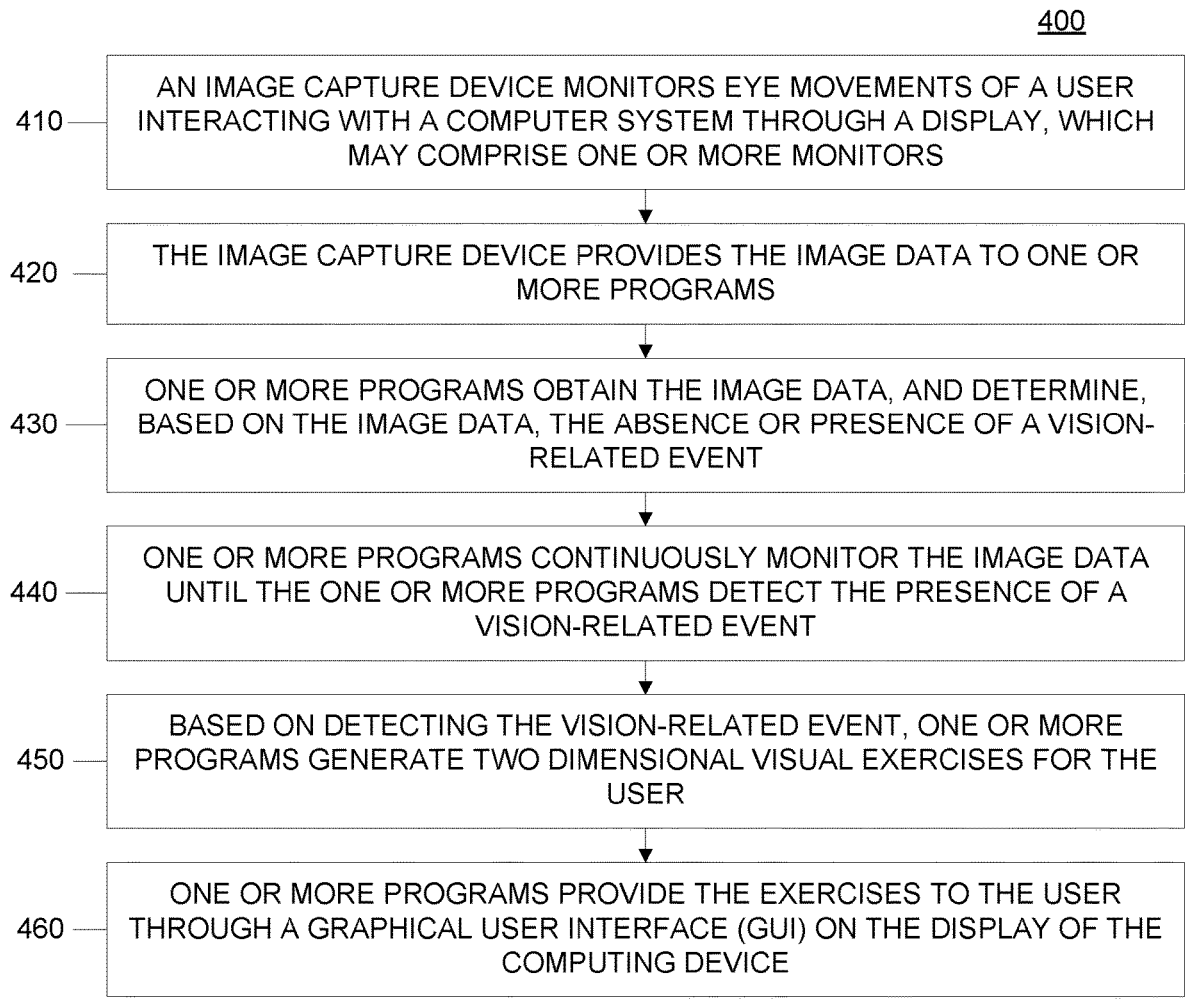
FIG. 4 is a workflow illustrating certain aspects of an embodiment of the present invention.

FIG. 4 is a general workflow 400 that illustrates certain aspects of some embodiments of the present invention. In some embodiments of the present invention, an image capture device monitors eye movements of a user interacting with a computer system through a display, which may comprise one or more monitors (410). The image capture device provides the image data to one or more programs (420). One or more programs obtain the image data, and determine, based on the image data, the absence or presence of a vision-related event (430).

A vision related event may include the one or more programs assigning a score to the user, based on the image data, where the score exceed a pre-determined threshold and the one or more programs generate the score based on parameters identified in the image data, including but not limited to, the consecutive time spent in front of a screen by the user without taking a break, the type of activity engaged in by the user, through the GUI on the computer screen, the time of day the user is engaging with a GUI on the computer screen, and the previous history of the user's utilization of the computer screen and/or eye movements during utilization of the computer screen. A vision related event may include the one or more programs determining, based on the image data, that a current focal point of the user differs from a focal point located at the level of the screen, which would be a correct focal point for a user who is not experiencing a vision-related issue.

Returning to FIG. 4, the one or more programs continuously monitor the image data until the one or more programs detect the presence of a vision-related event (440). Based on detecting the vision-related event, the one or more programs generate two dimensional visual exercises for the user (450) and provide the exercises to the user through a graphical user interface (GUI) on the display of the computing device (460).

Embodiments of the present invention include a computer-implemented method, a computer program product, and a computer system, in which one or more programs utilize an image capture device to track eye movements of a user interacting with a display communicatively coupled to the one or more processors, the image capture device continuously collecting image data. The one or more programs determine, based on analyzing the collected image data, a probability of whether a user may be experiencing a vision-related issue. The one or more programs, based on the probability being within a given pre-determined range, identify the vision-related issue experienced by the user. The one or more programs generate, based on the vision-related issue, a two dimensional visual exercise to address the vision-related issue for performance by the user. The one or more programs deploy a graphical user interface to the display, wherein the graphical user interface comprises the visual exercise. The one or more programs provide the visual exercise to the user via the graphical user interface.

In some embodiments of the present invention, the probability includes a score representing a likelihood that the user interacting with the display is experiencing the vision-related issue and where the pre-determined range comprises scores above a pre-determined threshold, where the one or more programs determining the probability includes: the one or more programs generating a score based on a group of parameters related to the collected image data and to personal information of the user.

In some embodiments of the present invention, the parameters related to the collected image data are selected from the group consisting of: eye movements of the user, continuous time spent in front of the computer monitor by the user, type of activity the user is engaged in while interacting with the display, and time of day in which the user is interacting with the display.

In some embodiments of the present invention, the parameters related to the personal information of the user comprise historical medical prescription information. This historical medical prescription information may include vision-related prescriptions issued to the user.

In some embodiments of the present invention, the threshold is based on the vision-related prescriptions issued to the user.

In some embodiments of the present invention, the vision-related issue includes convergence insufficiency.

In some embodiments of the present invention, the one or more programs identifying the convergence insufficiency includes the one or more programs computing, based on the collected image data, a distance between a focal point of the user the user and a correct focal point on the display. The correct focal point may be located at screen level of the display.

In some embodiments of the present invention, the one or more programs generating the two dimensional visual exercise to address the convergence insufficiency includes: the one or more programs generating an exercise to move a current focal point of the user from the focal point of the user to the correct focal point, where the exercise commences by setting the current focal point at the focal point of the user and redirecting a focus of the user by moving the current focal point toward the correct focal point by gradually decreasing a distance between the current focal point and the correct focal point.

In some embodiments of the present invention, the one or more programs providing the visual exercise to the user via the graphical user interface further comprises the one or more programs pausing or terminating an application the user us interacting with in the display.

In some embodiments of the present invention, the one or more programs also utilize the image capture device to track eye movements of the user interacting with the graphical user interface rendered in the display during the exercise, the image capture device continuously collecting additional image data. The one or more programs determine, based on the additional image data, that the user has completed the exercise. The one or more programs resume the application.

In some embodiments of the present invention, the image capture device includes a camera integrated into the display.

Referring now to FIG. 5, a schematic of an example of a computing node, which can be a cloud computing node 10. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove. In an embodiment of the present invention, the computing resources executing the one or more programs that generate vision exercises (among other aspects discussed) can be understood as one or more cloud computing nodes 10 (FIG. 5) and if not examples of a cloud computing node 10, then one or more general computing nodes that include aspects of the cloud computing node 10.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 12 that can be utilized as cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs). Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter). Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
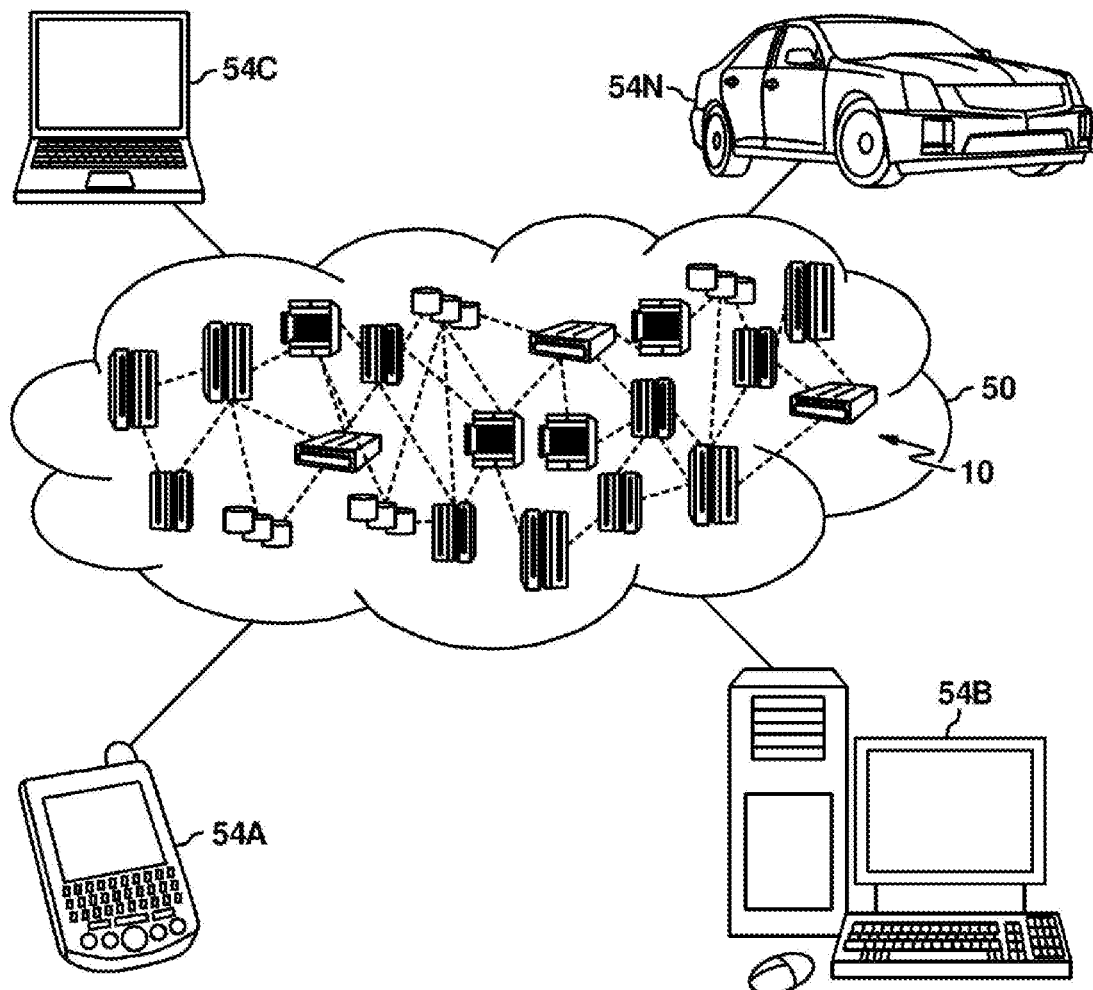
FIG. 6 depicts a cloud computing environment according to an embodiment of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
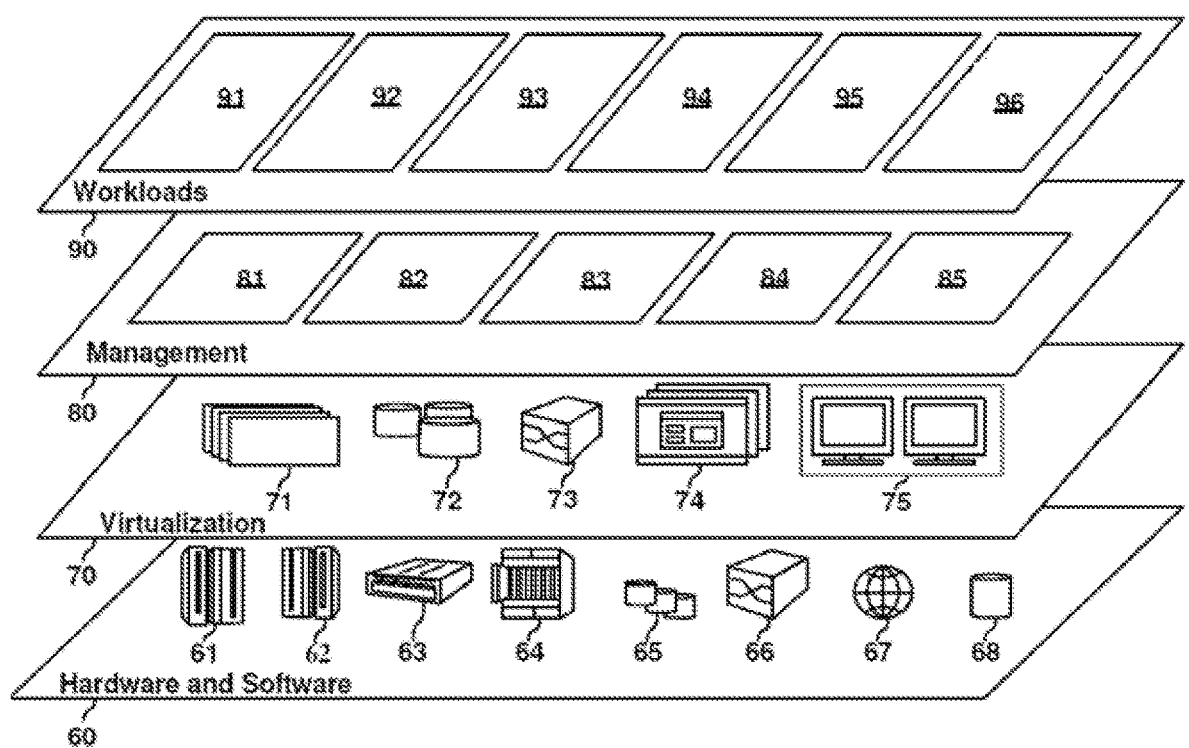
FIG. 7 depicts abstraction model layers according to an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and determining a probability of a vision-related issue of a computer user 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A computer-implemented method, comprising:
   utilizing, by one or more processors, an image capture device to passively track eye movements of a user interacting with a display communicatively coupled to the one or more processors, the display located at a distance from the user, while the user is reading textual content on the display from an application, the image capture device continuously collecting image data;
   determining, by the one or more processors, based on analyzing the collected image data, a probability of whether a user may be experiencing a vision-related issue;
   based on the probability being within a given pre-determined range, identifying, by the one or more processors, the vision-related issue experienced by the user;
   generating, by the one or more processors, based on the vision-related issue, a two dimensional visual exercise to address the vision-related issue for performance by the user, wherein an additional application comprises the visual exercise;
   deploying, by the one or more processors, a graphical user interface to the display, wherein the graphical user interface comprises the visual exercise; and
   providing, by the one or more processors, the visual exercise to the user via the graphical user interface, wherein providing the visual exercise comprises pausing the application from which the user is reading the textual content from in the display and resuming the application based on determining that the user has completed the visual exercise in the additional application.

2. The computer-implemented method of claim 1, wherein the probability comprises a score representing a likelihood that the user interacting with the display is experiencing the vision-related issue and wherein the pre-determined range comprises scores above a pre-determined threshold, wherein determining the probability comprises:
   generating, by the one or more processors, a score based on a group of parameters related to the collected image data and to personal information of the user.

3. The computer-implemented method of claim 2, where the parameters related to the collected image data are selected from the group consisting of: eye movements of the user, continuous time spent in front of the computer monitor by the user, type of activity the user is engaged in while interacting with the display, and time of day in which the user is interacting with the display.

4. The computer-implemented method of claim 2, where the parameters related to the personal information of the user comprise historical medical prescription information.

5. The computer-implemented method of claim 4, wherein the historical medical prescription information comprises vision-related prescriptions issued to the user.

6. The computer-implemented method of claim 5, wherein the threshold is based on the vision-related prescriptions issued to the user.

7. The computer-implemented method of claim 1, wherein the vision-related issue comprises convergence insufficiency.

8. The computer-implemented method of claim 7, wherein identifying the convergence insufficiency comprises computing, based on the collected image data and the distance from the user of the display, a distance between a focal point of the user the user and a correct focal point on the display.

9. The computer-implemented method of claim 8, wherein the correct focal point is located at screen level of the display.

10. The computer-implemented method of claim 8, wherein generating the two dimensional visual exercise to address the convergence insufficiency comprises:

generating, by the one or more processors, an exercise to move a current focal point of the user from the focal point of the user to the correct focal point, wherein the exercise commences by setting the current focal point at the focal point of the user and redirecting a focus of the user by moving the current focal point toward the correct focal point by gradually decreasing a distance between the current focal point and the correct focal point.

11. The computer-related method of claim 1, further comprising: utilizing, by one or more processors, the image capture device to track eye movements of the user interacting with the graphical user interface rendered in the display during the exercise, the image capture device continuously collecting additional image data; determining, by one or more processors, based on the additional image data, that the user has completed the exercise; and resuming, by the one or more processors, the application.

12. The computer-implemented method of claim 1, wherein the image capture device comprises a camera integrated into the display.

13. The computer-implemented method of claim 1, wherein the application and the additional application are separate applications.

* * * * *